United States Patent [19]

Archer

[11] Patent Number: 4,671,591
[45] Date of Patent: Jun. 9, 1987

[54] ELECTRICAL CONNECTOR
[75] Inventor: Michael F. Archer, Issaquah, Wash.
[73] Assignee: Physio-Control Corporation, Redmond, Wash.
[21] Appl. No.: 755,309
[22] Filed: Jul. 15, 1985
[51] Int. Cl.$^4$ .................. H01R 13/627; H01R 11/22
[52] U.S. Cl. ................................. 439/346; 128/641; 439/859
[58] Field of Search ................ 339/60 R, 60 C, 60 M, 339/61 R, 61 C, 61 M, 258 R, 29 B, 224, 228, 229, 261, 200 R, 200 P, 253 R, 253 F, 253 L, 253 S, 259 R, 259 F, 258 RR, 75 R; 128/641

[56] References Cited

U.S. PATENT DOCUMENTS

| | | | |
|---|---|---|---|
| 3,412,366 | 11/1968 | Pittman | 339/60 R |
| 3,750,094 | 7/1973 | Zenkich | 128/641 |
| 3,774,143 | 11/1973 | Lopin | 339/61 R |
| 4,072,388 | 2/1978 | Dunn | 128/641 |
| 4,178,052 | 12/1979 | Ekbom et al. | 339/61 R |
| 4,220,387 | 9/1980 | Biche et al. | 339/61 R |
| 4,390,223 | 6/1983 | Zenkich | 339/61 R |

FOREIGN PATENT DOCUMENTS 889632  9/1953  Fed. Rep. of Germany ...... 339/258 RR

Primary Examiner—Eugene F. Desmond
Assistant Examiner—Gary F. Paumen
Attorney, Agent, or Firm—Christensen, O'Connor, Johnson & Kindness

[57] ABSTRACT

A connector for establishing electrical connection between a conductor and a patient engaging electrode that includes a conductive post extending from the electrode. The post has a proximal portion, a distal portion, and an intermediate portion having a diameter smaller than the diameter of the distal portion. The connector comprises insulation means shaped to form a socket open at one end, a pair of first spring members, a pair of second spring members, and means for electrically connecting the conductor to the second spring members. The first spring members are laterally positioned with respect to one another in the socket, and the second spring members are laterally positioned with respect to one another in the socket closer to said one end than the first spring members. The first and second spring members are positioned and constructed such that when the post is inserted in the socket, the second spring members grip the proximal portion of the post, and the first spring members and the intermediate and distal portions of the post comprise a detent mechanism that resists removal of the post from the socket.

10 Claims, 7 Drawing Figures 4,671,591

ELECTRICAL CONNECTOR

FIELD OF THE INVENTION

The present invention relates to electrical connectors and, in particular, to a low-profile device for establishing electrical connection between a conductor and a conductive post extending from a patient engaging electrode.

BACKGROUND OF THE INVENTION

A number of electrical physiological instruments utilize electrodes that are applied directly to a patient's body. Examples of such instruments include defibrillators and pacemakers. In the past, a number of electrodes have been developed that have a low profile and that can remain adhesively attached to a patient over an extended period of time. Such electrodes must, of course, be connected to the defibrillator or other instrument when the electrodes are to be used. In the past, most low-profile defibrillation electrodes have been permanently attached to cables that terminate in a connector adapted to be plugged into the defibrillator or into a cable extending from the defibrillator. To increase the versatility and usefulness of disposable defibrillation electrodes, it would be desirable to provide a disposable defibrillation electrode having a small conductive post permanently affixed to the electrode, and to provide a connector whereby one end of a cable could be electrically connected to such post when the electrode was to be used. Prior disposable defibrillation electrodes have tended to avoid this approach, however, because of the difficulty in providing a connector that can handle the high currents used in defibrillation while at the same time having the low profile and reliability required for extended use.

SUMMARY OF THE INVENTION

The present invention provides a connector for establishing electrical connection between a conductor and a patient engaging electrode that includes a conductive post extending outward from the electrode. The post has a proximal portion, a distal portion, and an intermediate portion having a diameter smaller than the diameter of the distal portion. The connector comprises insulation means shaped to form a socket open at one end, a pair of first spring members, a pair of second spring members, and means for electrically connecting the conductor to the second spring members. The first spring members are laterally positioned with respect to one another in the socket, and the second spring members are laterally positioned with respect to one another in the socket and are positioned closer to said one end than the first spring members. The first and second spring members are arranged and constructed such that when the post is inserted through said one end into the socket, the second spring members grip the proximal portion of the post, and the first spring members and the intermediate and distal portions of the post comprise a detent mechanism that resists removal of the post from the socket.

DETAILED DESCRIPTION OF THE INVENTION

Figure 1:
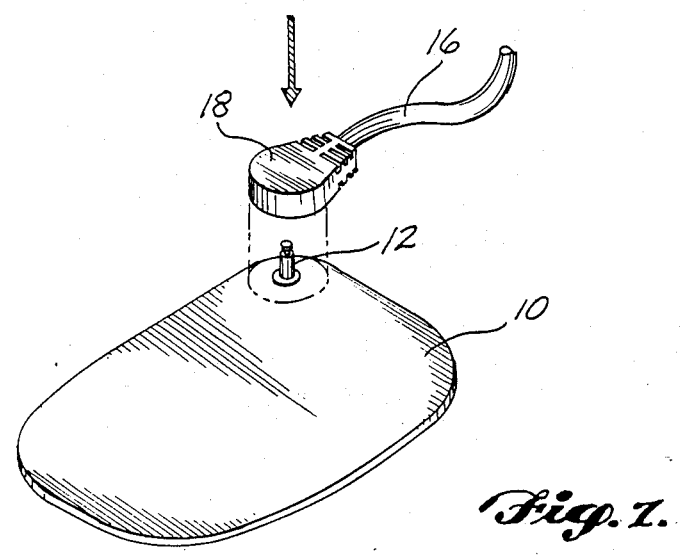
FIG. 1 is a perspective view of an electrode and a cable to which the electrode may be attached by means of the connector of the present invention.

FIG. 1 illustrates a disposable defibrillation electrode 10 that may be attached to cable 16 by means of connector 18 of the present invention. The lower surface (not shown) of electrode 10 comprises a conductive portion and an adhesively coated portion for fastening the electrode to a patient's skin. The upper surface of electrode 10 includes post 12 that is in electrical contact with the conductive section of the electrode. Post 12 may be connected to a defibrillator by means of cable 16 and connector 18 of the present invention. Cable 16 may comprise a single conductive line covered with a suitable insulating material.

Figure 2:
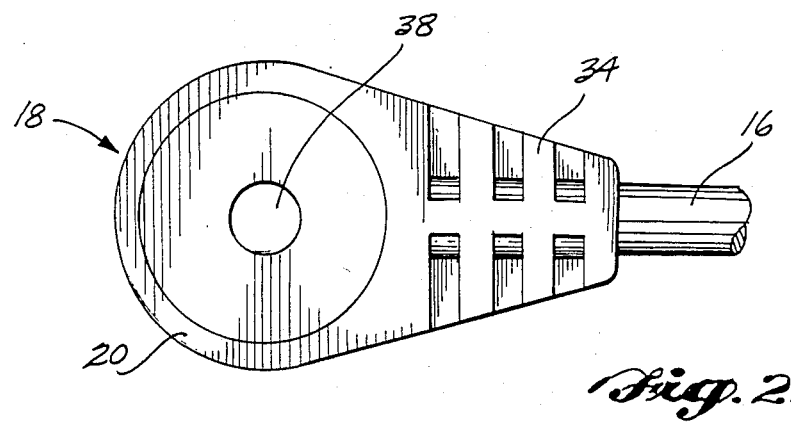
FIG. 2 is a bottom plan view of the connector of the present invention.
Figure 3:
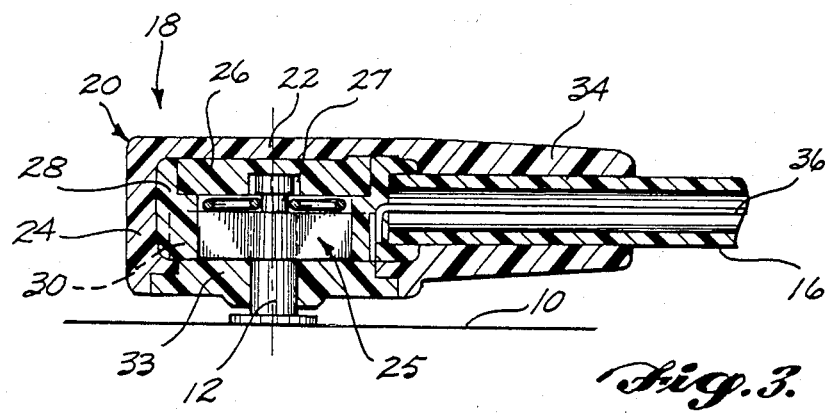
FIG. 3 is a cross-sectional view of the connector of FIG. 2.

Connector 18 is illustrated in greater detail in FIGS. 2 and 3. The connector comprises case 20 that includes upper wall 22 and cylindrical sidewall 24 that define and enclose cylindrical socket 25. Insulating disc 26 is adhesively secured to the underside of upper wall 22. Disc 26 serves as a stop to limit the movement of post 12 into socket 25, and includes central recess 27 to accommodate the upper end of the post. A cylindrical ring of mounting material 28 is positioned in socket 25 adjacent the inner surface of sidewall 24. Mounting material 28 mounts clip 30 such that the clip extends laterally along a diameter of socket 25. Mounting material 28 also mounts retainer spring 50 above clip 30. The functions of clip 30 and retainer spring 50 are described below. Strain relief 34 projects from one side of case 20, the strain relief being attached to the insulator covering of cable 16. Conductor 36 of cable 16 extends partially into socket 25, and makes connection with clip 30 as described below.

Connector 18 further includes protective covering 32 that extends across the lower end of connector 18. Protective covering 32 includes central opening 38 through which post 12 may be inserted, as indicated in FIG. 3. Protective covering 32 may comprise any suitable elastomeric insulating material such as a soft vinyl rubber. The protective coating functions to protect a person handling connector 18 from electric shock in the case of an accidental defibrillator discharge.

Figure 4:
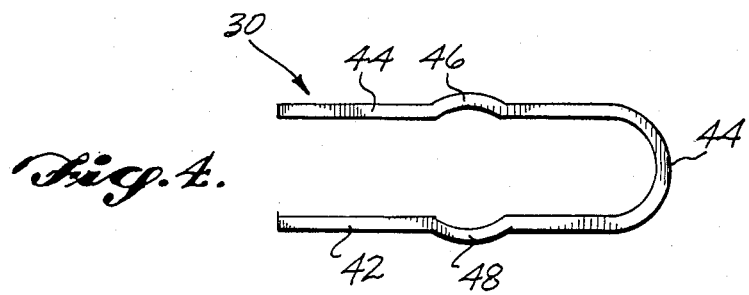
FIG. 4 is a top plan view of the clip.
Figure 5:
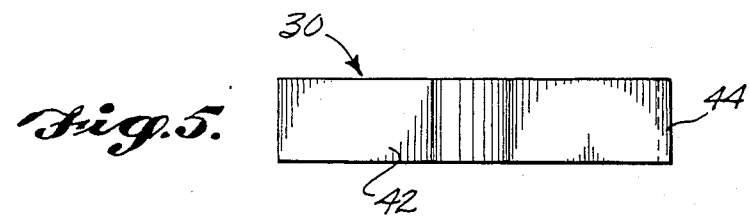
FIG. 5 is a side elevational view of the clip of FIG. 4.
Figure 6:
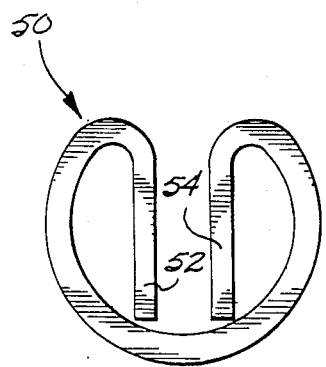
FIG. 6 is a top plan view of the retainer spring.

Referring now to FIGS. 4–6, clip 30 comprises a generally U-shaped metallic member having side sections 40 and 42 interconnected by intermediate section 44. Intermediate section 44 includes a 180° bend such that side sections 40 and 42 are parallel to but spaced apart from one another. Intermediate section 44 is electrically soldered to conductor 36 when the spring clip is installed in connector 18. Side sections 40 and 42 comprise a pair of lower spring members for making electrical contact with post 12, as described below. Side sections 40 and 42 include outwardly extending circular portions 46 and 48 respectively. Retainer spring 50 (FIG. 6) comprises a length of wire that is formed into the indicated, generally circular shape such that end sections 52 and 54 are parallel to and spaced from one another to form a pair of upper spring members for mechanically engaging the post.

Figure 7:
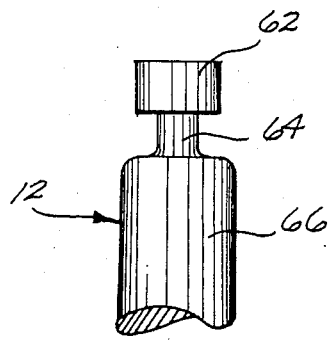
FIG. 7 is a side elevational view of the conductive post.

As best illustrated in FIG. 7, post 12 comprises distal portion 62, intermediate portion 64 and proximal portion 66, the terms "distal", "intermediate" and "proximal" referring to the relative positions of the respective portions with respect to electrode 10. FIG. 3 illustrates that when post 12 is inserted into socket 25 of connector 18, circular portions 46 and 48 of side portions 40 and 42 respectively grip and make electrical contact with proximal portion 66 of post 12, and end sections 52 and 54 of retainer spring 50 grip the post at intermediate portion 64. The end sections, together with distal portion 62 and intermediate portion 64, comprise a detent mechanism that resists removal of the post from the socket. Such a detent mechanism, however, does not compromise the electrical contact between side portions 42 and 44 and post 12. In particular, the inward travel of end sections 52 and 54 into contact with intermediate portion 64 does not reduce the spring tension exerted by the side portions against proximal portion 66. Circular portions 46 and 48 of side portions 40 and 42 are preferably selected to have a radius of curvature equal to the radius of curvature of proximal portion 66, to provide as large an area as possible for electrical contact.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A connector for establishing electrical connection between a conductor and a patient engaging electrode that includes a conductive post extending outward from the electrode, the post having a proximal portion, a distal portion, and an intermediate portion between the proximal and distal portions, the intermediate portion having a diameter smaller than the diameter of the distal portion, the connector comprising:
    insulation means shaped to form a socket having one end through which the post can be inserted into the socket;
    a first spring positioned in the socket;
    an electrically conductive second spring positioned in the socket closer to said one end than the first spring;
    the first and second springs not being unitary with each other being positioned and constructed such that when the post is inserted through said one end into the socket, the second spring operates independently of the first spring to engage the proximal portion of the post and establish electrical contact between the second spring and the post, and the first spring and the intermediate and distal portions of the post comprise a detent mechanism that operates independently of the second spring to resist removal of the post from the socket; and
    means for electrically connecting the conductor to the second spring.

2. The connector of claim 1, wherein the second spring comprises a generally U-shaped metallic member having first and second side sections and a bend of approximately 180° between the first and second side sections such that the side sections are spaced apart from and generally parallel to one another.

3. The connector of claim 2, wherein the first spring comprises a length of wire having a generally circular shape and having end sections that are parallel to and spaced apart from one another.

4. The connector of claim 1, wherein the first spring comprises a pair of spaced-apart first spring parts and resilient means for holding the first spring parts at predetermined positions within the socket and for resisting movement of the first spring parts away from said predetermined positions, wherein the first spring parts at said predetermined positions are spaced apart from one another by a distance less than the diameter of the distal portion of the post, and wherein when the post is inserted through said one end into the socket, the first spring parts are positioned on opposite sides of the intermediate portion of the post from one another to thereby cooperate with the intermediate and distal portions of the post to form the detent mechanism.

5. The connector of claim 4, wherein the socket has a substantially fixed size and shape, and wherein the first and second springs are mounted at substantially fixed positions within the socket.

6. A system for delivering electrical energy from a conductor to a patient, comprising:
    a patient-engaging electrode that includes a conductive post extending outward from the electrode, the post having a proximal portion, a distal portion, and an intermediate portion between the proximal and distal portions, the intermediate portion having a diameter smaller than the diameter of the distal portion;
    insulation means shaped to form a socket having one end through which the post can be inserted into the socket;
    a first spring positioned in the socket;
    an electrically conductive second spring positioned in the socket closer to said one end than the first spring;
    the first and second springs not being unitary with each other being positioned and constructed such that when the post is inserted through said one end into the socket, the second spring operates independently of the first spring to engage the proximal portion of the post and establish electrical contact between the second spring and the post, and the first spring and the intermediate and distal portions of the post comprise a detent mechanism that operates independently of the second spring to resist removal of the post from the socket; and
    means for electrically connecting the conductor to the second spring.

7. The connector of claim 6, wherein the second spring comprises a generally U-shaped metallic member having first and second side sections and a bend of approximately 180° between the first and second side sections such that the side sections are spaced apart from and generally parallel to one another.

8. The connector of claim 7, wherein the first spring comprises a length of wire having a generally circular shape and having end sections that are parallel to and spaced apart from one another.

9. The connector of claim 6, wherein the first spring comprises a pair of spaced-apart first spring parts and resilient means for holding the first spring parts at predetermined positions within the socket and for resisting movement of the first spring parts away from said predetermined positions, wherein the first spring parts at said predetermined positions are spaced apart from one another by a distance less than the diameter of the distal portion of the post, and wherein when the post is inserted through said one end into the socket, the first spring parts are positioned on opposite sides of the intermediate portion of the post from one another to thereby cooperate with the intermediate and distal portions of the post to form the detent mechanism.

10. The connector of claim 9, wherein the socket has a substantially fixed size and shape, and wherein the first and second springs are mounted at substantially fixed positions within the socket.

* * * * *